United States Patent
Moffatt

(10) Patent No.: US 6,767,640 B2
(45) Date of Patent: Jul. 27, 2004

(54) ANTI-OZONANTS COVALENTLY ATTACHED TO SILICA GEL FOR USE IN GLOSSY PRINT MEDIA

(75) Inventor: John R Moffatt, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/244,127

(22) Filed: Sep. 13, 2002

(65) Prior Publication Data

US 2004/0052949 A1 Mar. 18, 2004

(51) Int. Cl.$^7$ .......................... B32B 18/00; B32B 29/00
(52) U.S. Cl. ................... 428/446; 428/405; 428/452; 556/413; 556/424; 528/34; 427/387
(58) Field of Search .................. 528/28, 34; 556/413, 556/424; 428/446, 452

(56) References Cited

U.S. PATENT DOCUMENTS

| | | | |
|---|---|---|---|
| 3,627,800 A | * 12/1971 | Owen et al. ................ 556/424 |
| 3,849,178 A | 11/1974 | Feldman | |
| 3,968,074 A | 7/1976 | Schwarze et al. | |
| 5,149,839 A | * 9/1992 | Waketa et al. ............... 556/413 |
| 5,275,867 A | 1/1994 | Misuda et al. ............... 428/195 |
| 5,463,178 A | 10/1995 | Suzuki et al. ................ 428/216 |
| 5,576,088 A | 11/1996 | Ogawa et al. ............... 428/327 |
| 5,605,750 A | 2/1997 | Romano et al. ............ 428/304.4 |
| 5,908,723 A | * 6/1999 | Malhotra et al. ............. 430/31 |
| 5,989,378 A | 11/1999 | Liu et al. .................... 156/241 |
| 6,187,430 B1 | 2/2001 | Mukoyoshi et al. ........ 428/331 |

FOREIGN PATENT DOCUMENTS

WO    WO 200004029 A2 *  1/2000  .......... C07F/07/00

* cited by examiner

*Primary Examiner*—Margaret G. Moore
*Assistant Examiner*—Marc S Zimmer

(57) ABSTRACT

A method of protecting dyes printed on print media against ozonolysis is provided. The method comprises: (a) providing a first reaction product comprising the reaction of a phenylenediamine or derivative thereof (an anti-ozonant) with a silica or silicate; and (b) reacting the first reaction product in the presence of a water-free solvent with silica groups to form a second reaction product. Also provided is the reaction product resulting from the reaction of (1) the anti-ozonant-silica (or silicate) and (2) silica groups on a substrate. The anti-ozonant-silica (or silicate) is covalently attached to the particles of silica in the media and cannot escape or evaporate away. The use of phenylenediamines as anti-ozonants solves the problem of the fading of dyes on porous media by ozone pollution.

21 Claims, No Drawings

ANTI-OZONANTS COVALENTLY ATTACHED TO SILICA GEL FOR USE IN GLOSSY PRINT MEDIA

TECHNICAL FIELD

The present invention relates generally to ink jet printing, and, more particularly, to protection of ink jet images printed on print media against oxidation by ozone.

BACKGROUND ART

Oxidation of ink jet images printed on print media by ozonation is becoming more recognized as a problem, now that more pressing issues, such as water fastness and smear fastness, have been largely resolved. The problem of ozonation is particularly significant in urban areas where there are large concentrations of ozone from pollution, e.g., Los Angeles and Denver (during the summer months). That dyes and pigments react and thus decompose from ozone is a well-established fact.

Preventing oxidation by ozonation has not, however, been the subject of much investigation to date. Thus, there have been no prior solutions to this problem, to the best knowledge of the present inventor.

Thus, there is a need for preventing oxidation by ozonation of ink jet images printed on print media.

DISCLOSURE OF INVENTION

In accordance with embodiments disclosed herein, a method of protecting colorants printed on print media against ozonolysis is provided. The method comprises:

(a) providing a first reaction product comprising the reaction of a phenylenediamine or derivative thereof with a silane; and (b) reacting the first reaction product in the presence of a water-free solvent with silica groups to form a second reaction product.

Further in accordance with other embodiments disclosed herein, a reaction product is provided resulting from the reaction of (1) the first reaction product comprising the reaction of a phenylenediamine or derivative thereof with the silanol to form a phenylenediamine silane (or phenylenediamine silanol) and (2) silica groups on a substrate.

Additionally, in accordance with yet other embodiments disclosed herein a method of printing an ink on a print media is provided, where the ink contains at least one colorant susceptible to ozonolysis. The method comprises:

(a) providing a first reaction product comprising the reaction of a phenylenediamine or derivative thereof with a silane;

(b) reacting the first reaction product in the presence of a water-free solvent with silicic acid groups on the silica gel coated media to form a second reaction product, namely, a PDA-derivatized silica gel; and (c) printing the ink on the print media.

The anti-ozonant employed in accordance with the teachings herein is covalently attached to the particles of PDA-derivatized silica gel in the media and cannot escape or evaporate away.

The use of phenylenediamines, or derivatives thereof, solves the problem of the fading of dyes on porous media by ozone pollution.

BEST MODES FOR CARRYING OUT THE INVENTION

It is well known in the plastics and rubber technologies fields that phenylenediamines (PDAs) and like amines are excellent ozonolysis inhibitors. They react with ozone and other oxidants at a much faster rate than the unsaturated links in the polymer and afford protection to the polymer from these oxidants. They have the following structure:

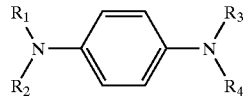

where $R_1$, $R_2$, $R_3$, and $R_4$ are independently alkyl, aryl, alkene, or arene groups, branched chain or straight chain or any combination thereof, comprising 30 carbon atoms or less, with the proviso that while any two R groups can be aryl, there are no more than two aryl groups. Of the alkyl groups, the secondary alkyls (2-alkyls or iso-alkyls) are most effective in preventing ozone degradation.

The rates of reaction of a variety of compounds, including three derivatives of phenylenediamine (PDA), with ozone are summarized in the Table below:

TABLE

Rates of Reaction for Various Compounds with Ozone

| Compound | Rate of Reaction, $10^5 \, k \cdot M^{-1} \cdot s^{-1}$ |
| --- | --- |
| N,N'-diisopentyl-p-PDA | 80 |
| N,N'-di-n-octyl-p-PDA | 70 |
| N-phenyl-N'-isopropyl-p-PDA | 70 |
| N-butyl-N,N'-dibutylthiourea | 20 |
| cis-polyisoprene | 4.4 |
| cis-polybutadiene | 0.6 |

It is seen that the PDA derivatives react with ozone considerably faster than other compounds.

Attaching PDA derivatives to print media used for ink jet printing renders the inks printed thereon substantially immune to ozonation; that is, the printing media that contains colorants printed thereon is rendered non-ozone fugitive. Thus, PDA derivatives when incorporated in an alkyl backbone attached to silicic acid groups on the silica gel coated media would afford such protection against colorant fugitive agents.

The embodiments disclosed herein are directed to the synthesis, dispersal, and printing use of these PDA-derivatized silica gels present in the print media.

A two-step reaction is involved. In the first step, a PDA-silanating reagent is prepared with the anti-ozonant molecule covalently attached to it. The preparation of such PDA-silane derivatives is known in the prior art. In the second step, the reaction of the PDA-silanating reagent with the silicic acid groups on the silica gel coating on the media surface results in the formation of a PDA-derivatized silica gel. Specifically, this second reaction is a simple one to carry out. The coupling occurs at room temperature over a few hours in an alcohol-based solvent, usually methanol. Stoichiometric quantities of reagent are sometimes used, and sometimes they are not—it depends on the application. Separation occurs readily, since the silica gel is insoluble in the solvent. Purification is easily performed by washing the silica particles with excess, clean methanol. (These methods are well appreciated in chromatography, such as silating a column to change its properties, for example.)

When ozone encounters such PDA-modified silica gel coatings on the media in the presence of dye molecules, the ozone reacts with the derivative rather than with the dye molecule, thus saving the dye molecule from ozonolysis.

The same reaction occurs with pigments, but to a lesser extent. It appears that, due to the number of pigment molecules in a pigment crystal, a large number of pigment chromophore molecules may be lost before there is a significant decrease in optical density. Nevertheless, the benefits of the embodiments disclosed herein are applicable to both dyes and pigments, which generically fall within the term "colorant".

Examples of PDA-silane derivatives that may be employed in the practice of the embodiments disclosed herein include, but are not limited to, the following compounds:

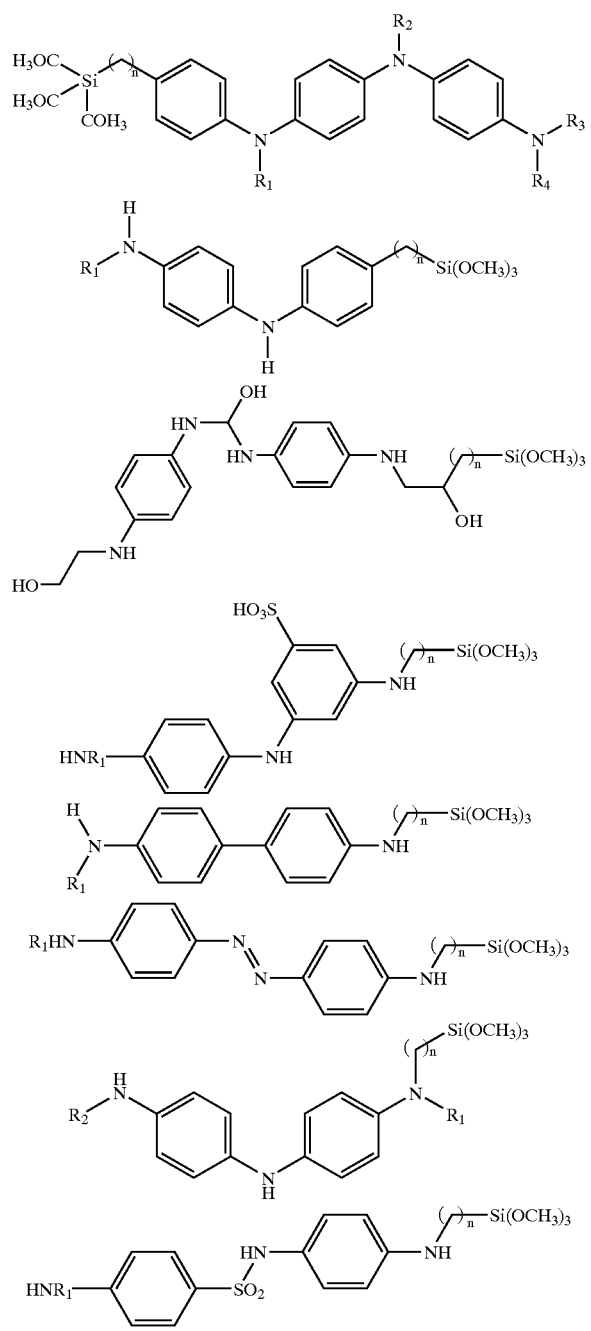

where $R_1$, $R_2$, $R_3$, and $R_4$ are independently any alkyl, alkene, arene, or aromatic group and where n is from 1 to 10. Essentially, the same requirements obtain for the R groups as listed above.

In the second step, the PDA-silane is attached to silicic acid groups on the silica gel coated surface of the print media via a silicon oxide coupling that is well-known in the prior art to form a PDA modified silica gel coating. Simply selecting one of the PDA silanes) or PDA silanols) from the list herein and reacting it with the silicic acid groups on the silica gel coating (on the print media) in the absence of water, e.g., employing absolute methanol as the reaction solvent yields the desired PDA-derivatized silica gel.

The second reaction may be illustrated as follows:

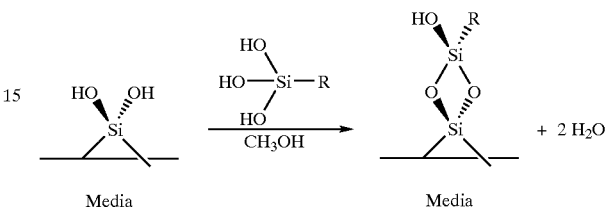

where R is the phenylenediamine moiety (or PDA derivative).

The print media employed in conjunction with the teachings herein is essentially plain paper provided with one or more coatings of silica gel to provide a glossy print medium. Such print media are used in color ink jet printing to provide the equivalent of photographic prints.

It is possible to react the silica gel first and then coat the paper with the reaction product. However, it is preferable to complete the reagent first and then perform the coupling on the PDA silane with the silicic acid groups on the silica gel on the print media. That ensures that the PDA-derivatized silica gel is where the attachment is, as opposed to being only on the other components of the print media. It is desirable to maximize the amount on the surface of the print media for the maximal effect.

Silica gel coatings on print media are disclosed elsewhere; see, e.g., U.S. Pat. Nos. 5,275,867; 5,463,178; 5,576,088; 5,605,750; 5,989,378; and 6,187,430, the contents of which are incorporated herein by reference. Typically, plain paper (the substrate) or a lower layer is coated with a proprietary mixture of silica, binder, such as poly(vinyl alcohol), and other components.

INDUSTRIAL APPLICABILITY

Thus, there have been disclosed methods and compounds for protecting dyes printed on print media against ozonolysis.

What is claimed is:

1. A method of protecting colorants printed on print media against ozonolysis comprising:

prior to printing an ink containing at least one said colorant on said print media, reacting a first reaction product in the presence of a water-free solvent with silicic acid groups on a silica gel coating on said print media to form a second reaction product;

wherein the first reaction product is prepared by the reaction of a phenylenediamine or derivative thereof with a silane.

2. The method of claim 1 further comprising the step of coating the second reaction product on a surface of the print media.

3. The method of claim 1 further comprising printing an ink on said print media, said ink including at least one colorant.

4. The method of claim 1 wherein said phenylenediamine comprises:

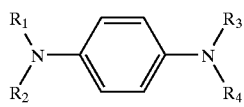

where $R_1$, $R_2$, $R_3$, and $R_4$ are independently selected from the group consisting of alkyl, aryl, alkene, and arene groups, whether branched chain or straight chain or any combination thereof, comprising 30 carbon atoms or less, with the proviso that while any two R groups can be aryl, there are no more than two aryl groups.

5. The method of claim 4 wherein said alkyl groups comprise secondary alkyls.

6. The method of claim 1 wherein said first reaction product is selected from the group consisting of

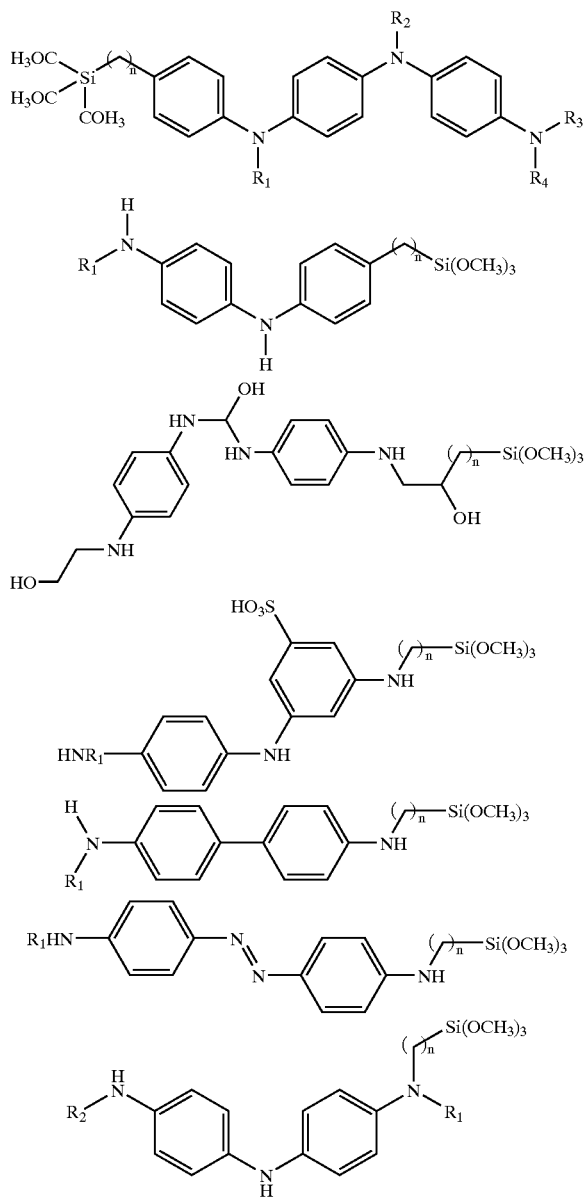

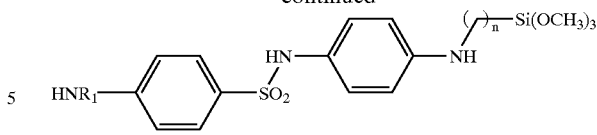

where $R_1$, $R_2$, $R_3$, and $R_4$ are independently an alkyl, alkene, arene, or aromatic group and where n is from 1 to 10.

7. The method of claim 1 wherein said colorant is a dye.

8. The method of claim 1 wherein said colorant is a pigment.

9. The method of claim 1 wherein said print media comprises plain paper provided with at least one coating layer containing silica gel.

10. A method of printing an ink on a print media, said ink containing at least one colorant susceptible to ozonolysis, said method comprising:

(a) reacting a first reaction product in the presence of a water-free solvent vent with silicic acid groups on a silica gel coating on said print media to form a second reaction product;

(b) printing said ink on said print media;

wherein the first reaction product comprises the reaction of a phenylenediamine or derivative thereof with a silane.

11. The method of claim 10 further comprising the step of coating the second reaction product on a surface of the print media.

12. The method of claim 10 wherein said phenylenediamine comprises:

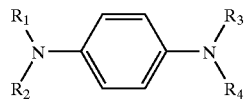

where $R_1$, $R_2$, $R_3$, and $R_4$ are independently selected from the group consisting of alkyl, aryl, alkene, and arene groups, whether branched chain or straight chain or any combination thereof, comprising 30 carbon atoms or less, with the proviso that while any two R groups can be aryl, there are no more than two aryl groups.

13. The method of claim 10 where said alkyl groups comprise secondary alkyls.

14. The method of claim 10 wherein said first reaction product is selected from the group consisting of

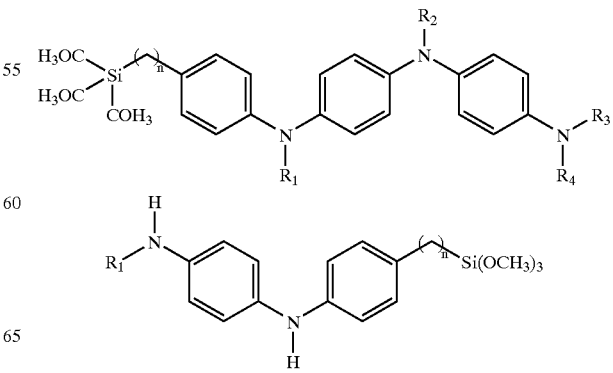

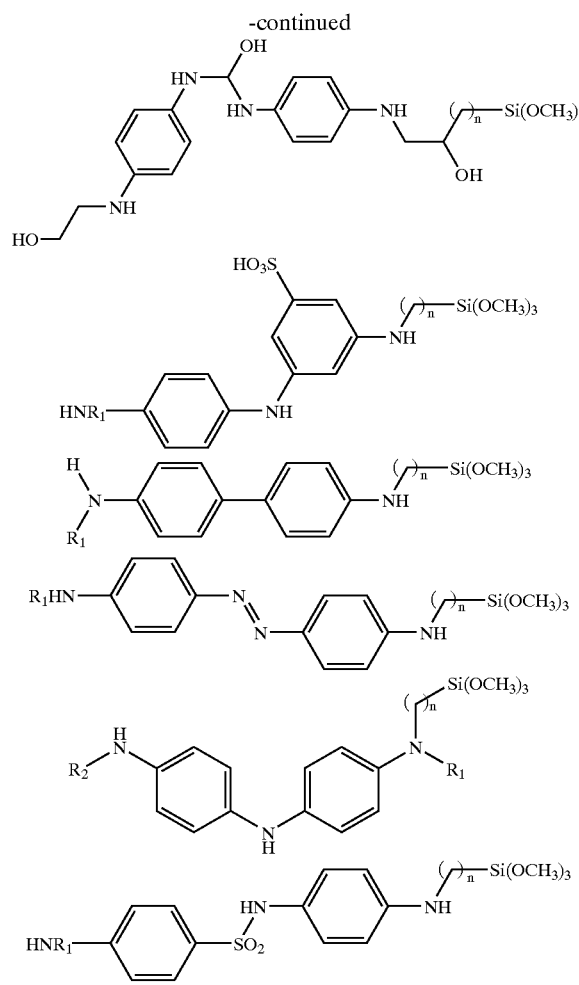

where $R_1$, $R_2$, $R_3$, and $R_4$ are independently an alkyl, alkene, arene, or aromatic group and where n is from 1 to 10.

15. The method of claim 10 wherein said colorant is a dye.

16. The method of claim 10 wherein said colorant is a pigment.

17. The method of claim 10 wherein said print media comprises plain paper provided with at least one coating layer containing silica.

18. A reaction product resulting from the reaction of (1) a first reaction product is prepared by the reaction of a phenylenediamine or derivative thereof with a silane and (2) silicic acid groups on a silica gel.

19. The reaction product of claim 18 wherein said phenylenediamine comprises:

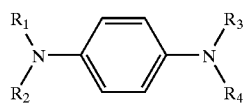

where $R_1$, $R_2$, $R_3$, and $R_4$ are independently selected from the group consisting of alkyl, aryl, alkene, and arene groups, whether branched chain or straight chain or any combination thereof, comprising 30 carbon atoms or less, with the proviso that while any two R groups can be aryl, there are no more than two aryl groups.

20. The reaction product of claim 19 wherein said alkyl groups comprise secondary alkyls.

21. The reaction product of claim 18 wherein said first reaction product is selected from the group consisting of

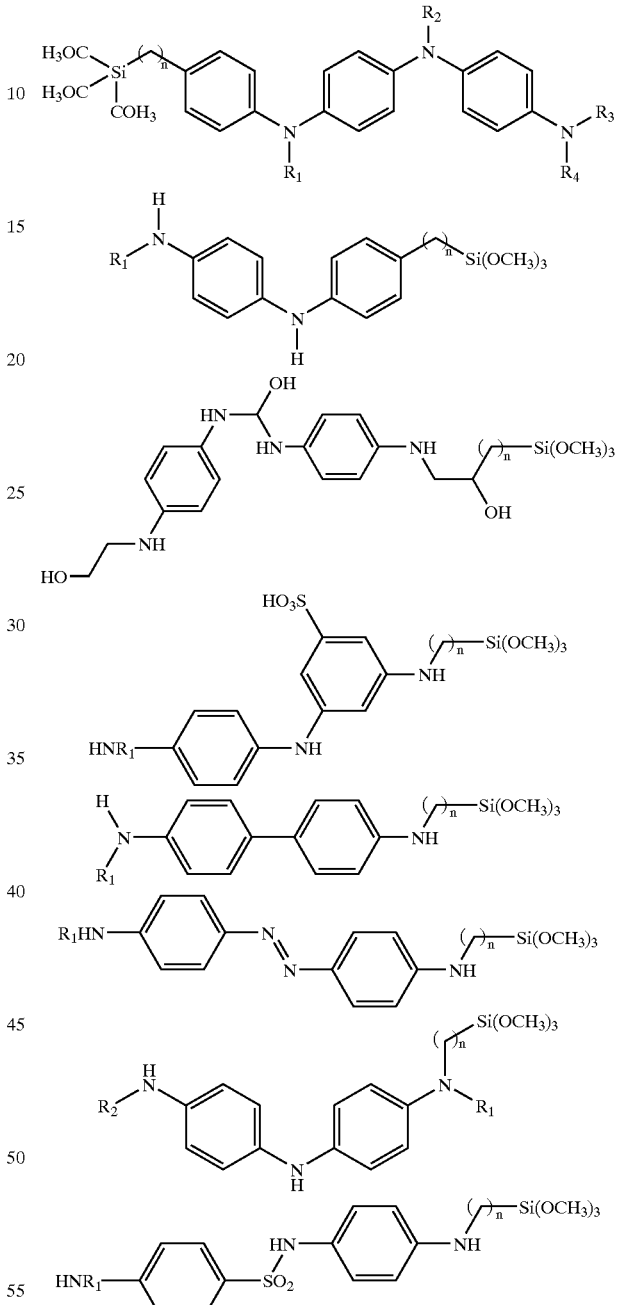

where $R_1$, $R_2$, $R_3$, and $R_4$ are independently an alkyl, alkene, arene, or aromatic group and where n is from 1 to 10.

* * * * *